United States Patent
Negm et al.

(10) Patent No.: US 11,845,750 B1
(45) Date of Patent: Dec. 19, 2023

(54) ANTIPROLIFERATIVE SELENATED-FOLATE HYBRIDS

(71) Applicant: KING FAISAL UNIVERSITY, Al-Ahsa (SA)

(72) Inventors: Amr Negm, Al-Ahsa (SA); Saad Shaaban, Al-Ahsa (SA); Yasair S. Al-Faiz, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/231,103

(22) Filed: Aug. 7, 2023

(51) Int. Cl.
  *C07D 475/04* (2006.01)
  *C12N 9/06* (2006.01)

(52) U.S. Cl.
  CPC ......... *C07D 475/04* (2013.01); *C12N 9/0028* (2013.01); *C12Y 105/01005* (2013.01); *C12Y 105/01015* (2013.01)

(58) Field of Classification Search
  CPC .................................................. C07D 475/04
  See application file for complete search history.

(56) References Cited

PUBLICATIONS

Rosemond-Hornbeak (Molecular Pharmacology, 14, 299-305 (1978)).*
Connelly-Frost et al., "Selenium, Folate, and Colon Cancer", Nutrition and Cancer, vol. 61, 2009—Issue 2, pp. 165-178.
Boss, "Development of Folate Receptor-Targeted Pet Radiopharmaceuticals for Tumor Imaging—A Bench-to-Bedside Journey", Jun. 2020, Cancers 12(6):1508.
Xia et al., "Folate-Targeted Selenium Nanoparticles Deliver Therapeutic Sirna to Improve Hepatocellular Carcinoma Therapy", RSC Adv., 2018, 8, 25932.

* cited by examiner

*Primary Examiner* — Valerie Rodriguez-Garcia
(74) *Attorney, Agent, or Firm* — Nath, Goldberg & Meyer; Richard C. Litman

(57) ABSTRACT

Novel organoselenium compounds formed with folates that can be used to maximize anticancer activity of the organoselenium. Novel organoselenium compounds that can be used as a chemopreventive against cancer. These compounds may be present in pharmaceutical compositions and may be used in various treatment methods.

10 Claims, No Drawings

ANTIPROLIFERATIVE SELENATED-FOLATE HYBRIDS

BACKGROUND

1. Field

The present disclosure provides novel organoselenium compounds formed with folates that can be used to maximize anticancer activity of the organoselenium.

2. Description of the Related Art

The cell membrane reduced folate carrier, SLC19A1, has a crucial role in intracellular folates transportation. Folates are necessary for the nucleotide and amino acids synthesis for cancer cells. Moreover, the enzymes methylenetetrahydrofolate dehydrogenase-cyclohydrolase 1 and 2 (MTHFD1 and MTHFD2) are very crucial for upregulating nucleotide synthesis pathway to fuel cancer cells with nucleotides.

Organoselenium agents manifest immense activities and potential applications. Recent studies revealed that organic selenide and diselenides exhibit preferential cellular growth inhibition towards cancer cells with higher selectivity. To date, no fused organosellenium compounds have been formed with folates.

The development of new organolselenium compounds formed with folates having a novel chemical structure for cancer therapy as well as pharmaceutical compositions containing the compound as an active ingredient have been desired. Thus, new cancer therapies solving the aforementioned problems are desired.

SUMMARY

The present disclosure relates to novel selenate-folate antagonists to promote the cellular uptake of organoselenium by facilitating their movement through SLC19A1 from outside the cell into the cytoplasm and maximize the anticancer activity of organoselenium compounds by blocking the action of folates by targeting MTHFD1 and MTHFD2 inhibition and increasing the cellular concentration of organoselenium. The subject matter of the present disclosure is expected not only to increase the cellular uptake but also to maximize the anticancer activity of organoselenium through MTHFD1 and MTHFD2 inhibition which leads to trapping folate that cause cell cycle arrest and cancer cell death.

Thus, the present disclosure provides novel organic selenide compounds that can be used as chemopreventive against cancer.

In an embodiment, the present subject matter relates to a compound having the formula 1:

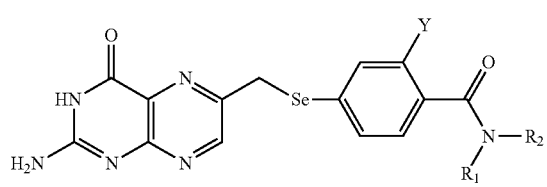

or a pharmaceutically acceptable salt, ester, stereoisomer, or solvate thereof, wherein:

Y is selected from the group consisting of hydrogen, fluorine, $NO_2$, methyl, and cyano; and $R_1$ is hydrogen and $R_2$ is selected from the group consisting of ethanedioic acid, (3-methylthio)propanoic acid, and propanedioic acid, or $R_1$ and $R_2$ are taken together with the nitrogen to which they are attached to form a proline.

In another embodiment, the present subject matter relates to a compound selected from the group consisting of:

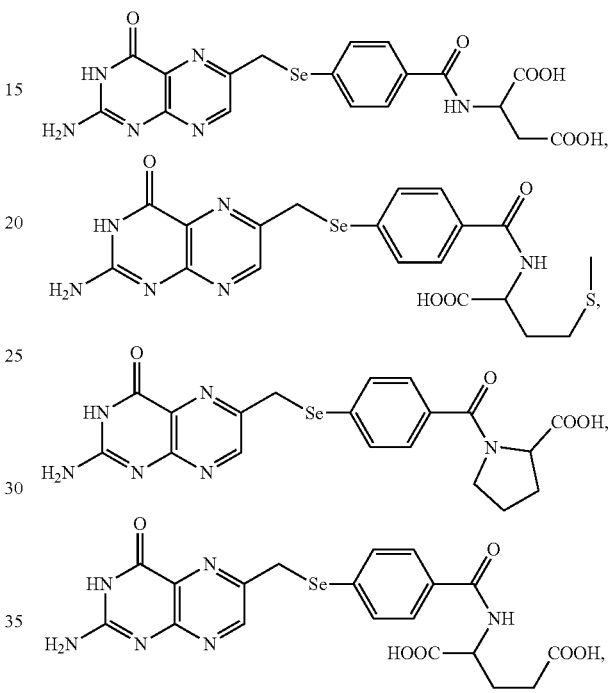

and a pharmaceutically acceptable salt, ester, stereoisomer, or solvate thereof.

In another embodiment, the present subject matter relates to a pharmaceutical composition comprising a therapeutically effective amount of a compound as described herein and a pharmaceutically acceptable carrier.

In an embodiment, the present subject matter relates to a method of treating a cancer in a patient, comprising administering to a patient in need thereof a therapeutically effective amount of a compound as described herein.

In another embodiment, the present subject matter relates to a method of inhibiting methylenetetrahydrofolate dehydrogenase-cyclohydrolase 1 or 2 (MTHFD1 or MTHFD2) activity in a patient, comprising administering to a patient in need thereof a therapeutically effective amount of a compound as described herein.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-C40 alkyl group), for example, 1-30 carbon atoms (i.e., C1-C30 alkyl group). In some embodiments, an alkyl group can have 1 to 6 carbon atoms, and can be referred to as a "lower alkyl group" or a "C1-C6 alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-C24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain 0-0, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkylxarylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula 1:

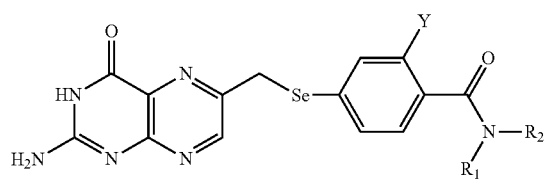

or a pharmaceutically acceptable salt, ester, stereoisomer, or solvate thereof, wherein:

Y is selected from the group consisting of hydrogen, fluorine, NO$_2$, methyl, and cyano; and R$_1$ is hydrogen and R$_2$ is selected from the group consisting of ethanedioic acid, (3-methylthio)propanoic acid, and propanedioic acid, or R$_1$ and R$_2$ are taken together with the nitrogen to which they are attached to form a proline.

In certain embodiments, the present subject matter relates to a compound of formula 1 having the formula I:

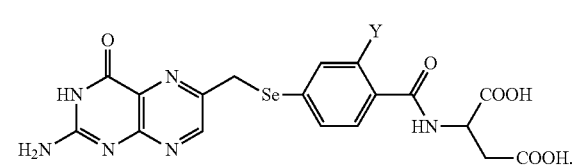

In other embodiments, the present subject matter relates to a compound of formula 1 having the formula II:

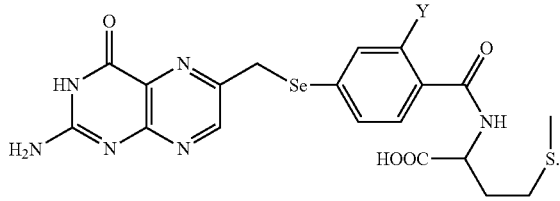

In further embodiments, the present subject matter relates to a compound of formula 1 having the formula III:

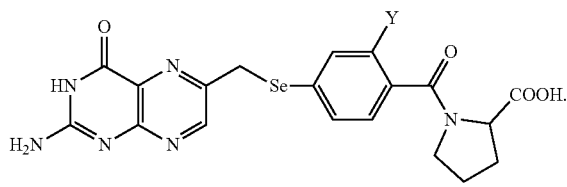

In additional embodiments, the present subject matter relates to a compound of formula 1 having the formula IV:

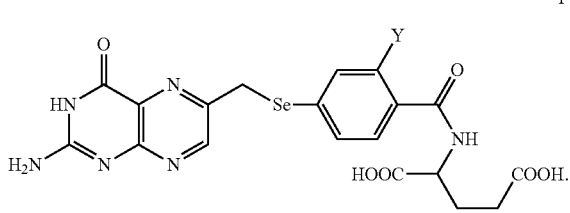

In another embodiment, the compound described herein can be selected from the group consisting of:

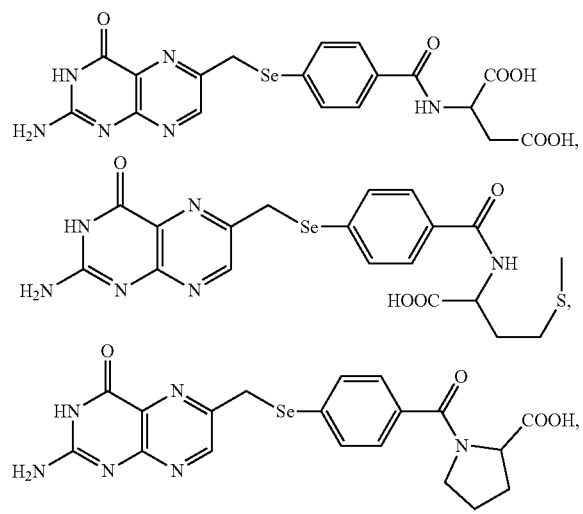

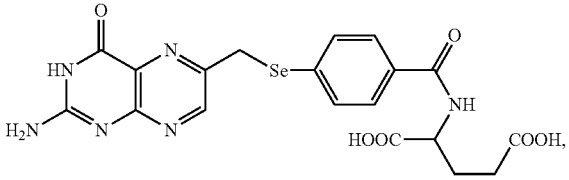

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula 1 and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula 1, as well as the solvates of the salts, the stereoisomers and the salts of the stereoisomers of the compounds of formula 1.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula 1 and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. First, an intermediate compound 4-(((2-amino-4-oxo-3,4-dihydropteridin-6-yl)methyl)selanyl)benzoic acid (3) can be synthesized by the reduction of 4,4'-diselanediyldibenzoic acid (2) using $NaBH_4$ under inert gas (including, by way of non-limiting example, $N_2$) in ethanol followed by subsequent reaction with 2-amino-6-(bromomethyl)pteridin-4 (3H)-one (1) via nucleophilic substitution strategy.

Then, a reaction of benzoic acid derivative 3 with oxalyl chloride in dichloromethane can afford the respective acid chloride, which in turn can react, in situ, with different amino acids, including by way of non-limiting example aspartic acid, L-methionine, glutamic acid, and proline to give the corresponding amides (4-(((2-amino-4-oxo-3,4-dihydropteridin-6-yl)methyl)selanyl)benzoyl)aspartic acid (4), (4-(((2-amino-4-oxo-3,4-dihydropteridin-6-yl)methyl)selanyl)benzoyl)methionine (5), (4-(((2-amino-4-oxo-3,4-dihydropteridin-6-yl)methyl)selanyl)benzoyl)glutamic acid (6), and (4-(((2-amino-4-oxo-3,4-dihydropteridin-6-yl)methyl)selanyl)benzoyl)proline (7), as shown in Schemes 1 and 2.

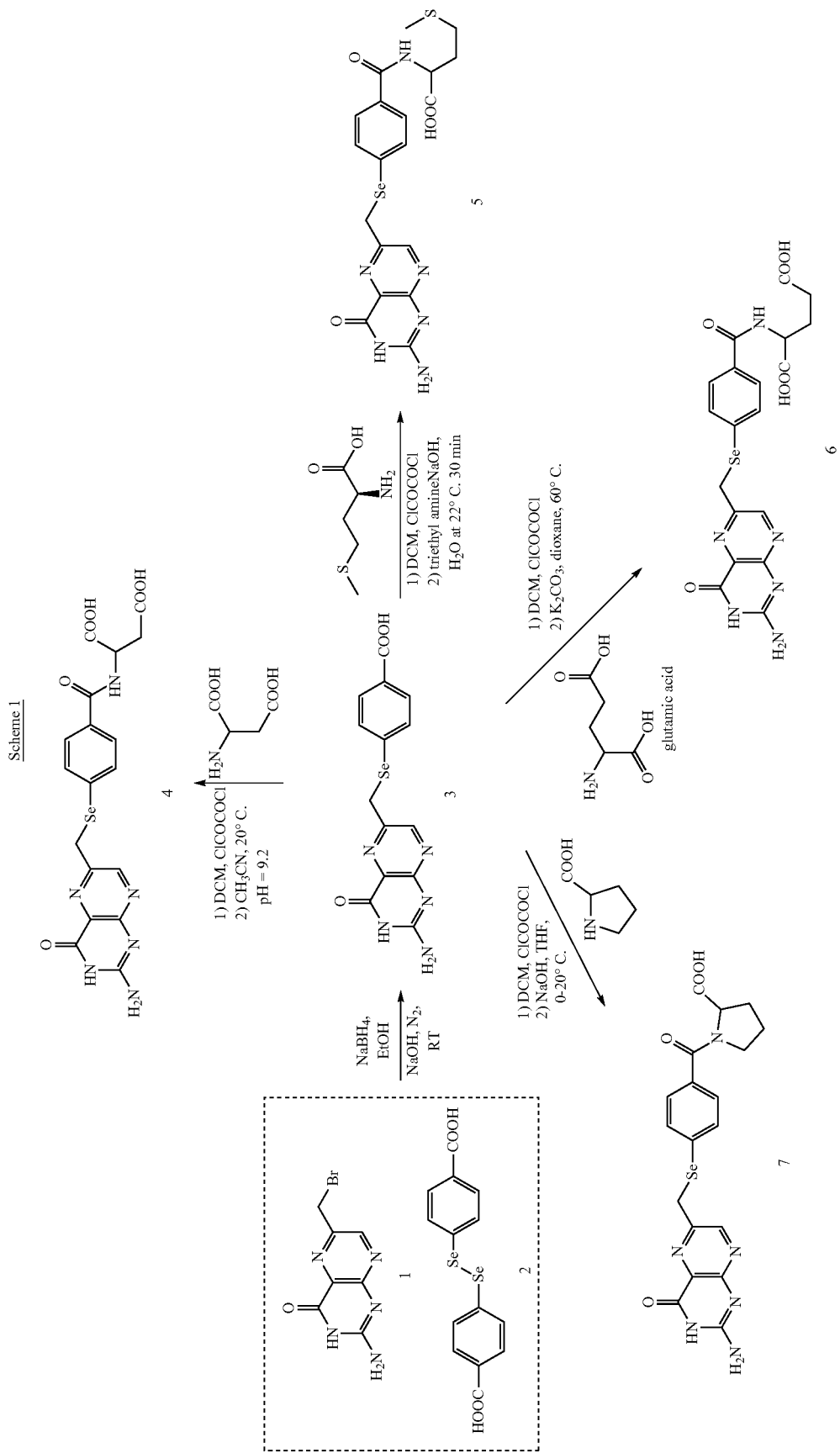

Scheme 2

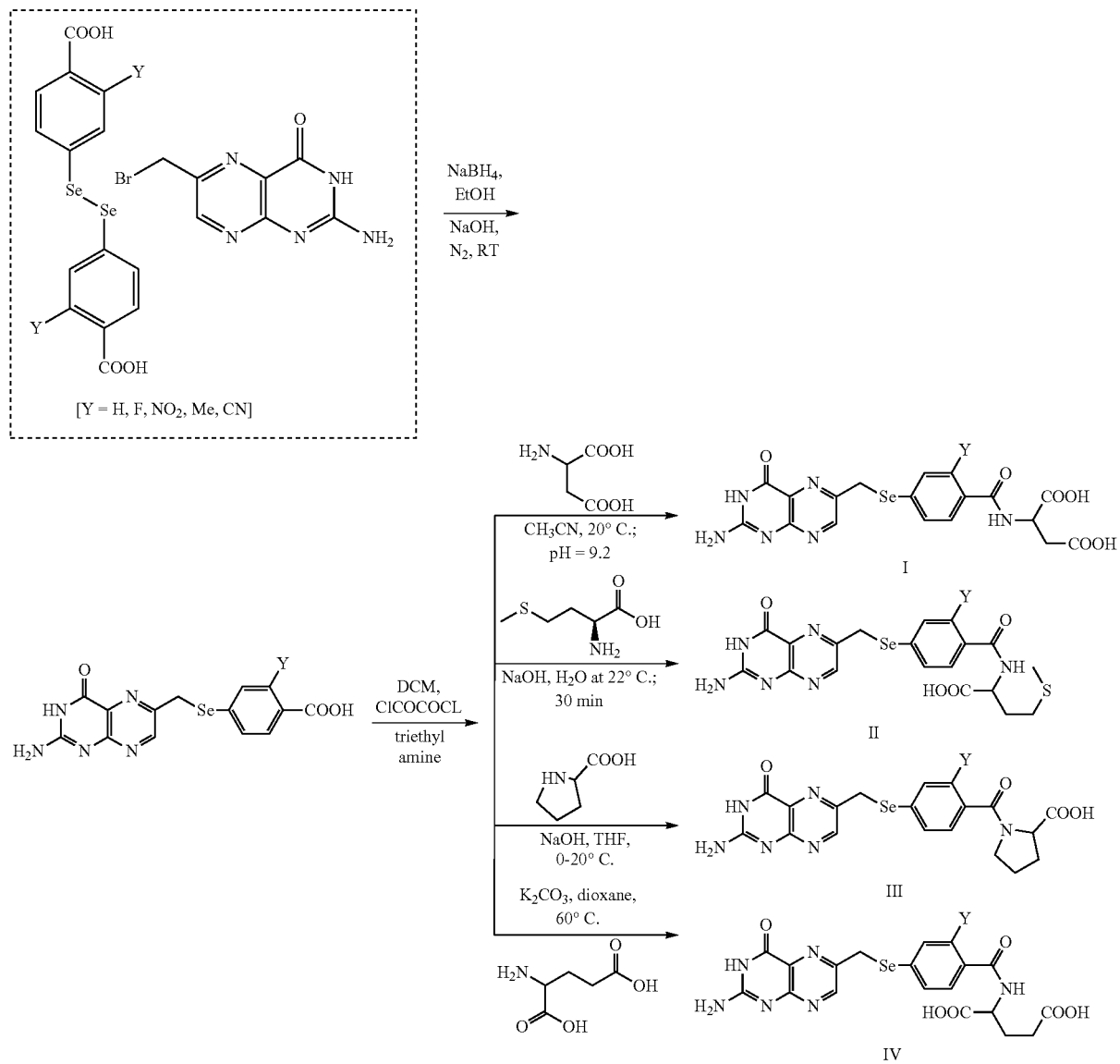

In another embodiment, the present subject matter relates to a pharmaceutical composition comprising a therapeutically effective amount of a compound as described herein and a pharmaceutically acceptable carrier.

In this regard, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein, or in combination therapy with another composition containing other components.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg, or even 100 µg/kg, of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction.

Another manner of administration is parenteral administration, generally characterized by injection, either subcutaneously, intramuscularly, intraperitoneally, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

The present compounds have valuable pharmaceutical properties, which make them commercially utilizable. Accordingly, the present subject matter further relates to use of the present compounds for the treatment of diseases such as cancers. Similarly, the present compounds can be used to inhibit methylenetetrahydrofolate dehydrogenase-cyclohydrolase 1 and/or 2 (MTHFD1 and/or MTHFD2) enzyme activity in a patient.

In an embodiment, the present subject matter relates to a method of treating a cancer in a patient, comprising administering to a patient in need thereof a therapeutically effective amount of a compound as described herein.

In one embodiment in this regard, the treating the cancer can include providing a chemopreventive effect to the patient who is at risk of developing the breast cancer.

In an additional embodiment, the present subject matter relates to a method of inhibiting methylenetetrahydrofolate dehydrogenase-cyclohydrolase 1 and/or 2 (MTHFD1 or MTHFD2) activity in a patient, comprising administering to a patient in need thereof a therapeutically effective amount of a compound as described herein.

In one embodiment in this regard, administration of the compound to the patient can lead to trapping a folate that causes cell cycle arrest and cancer cell death in the patient.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

In an embodiment of the present methods, the compound used in the methods can have the formula I:

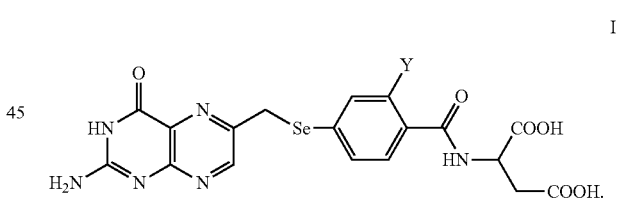

In another embodiment of the present methods, the compound used in the methods can have the formula II:

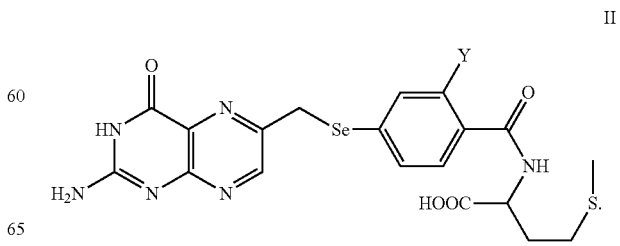

In a further embodiment of the present methods, the compound used in the methods can have the formula III:

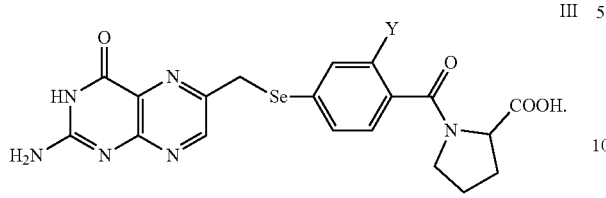

In a further embodiment of the present methods, the compound used in the methods can have the formula IV:

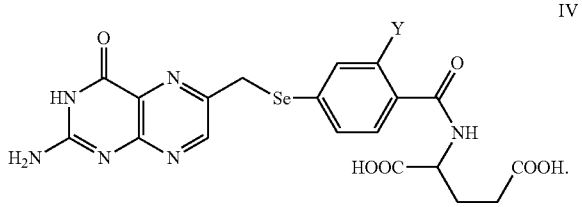

In an embodiment of the present methods, the compound used in the methods can be selected from the group consisting of:

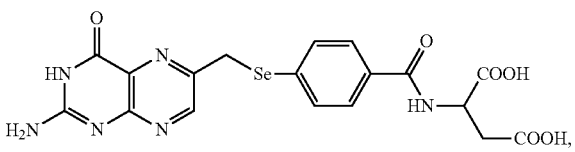

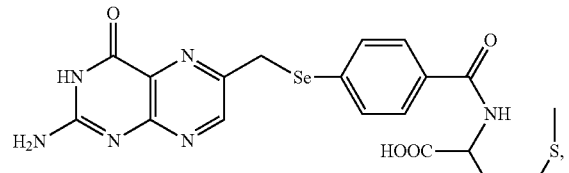

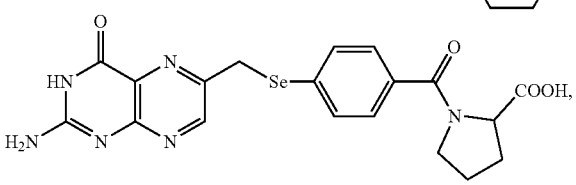

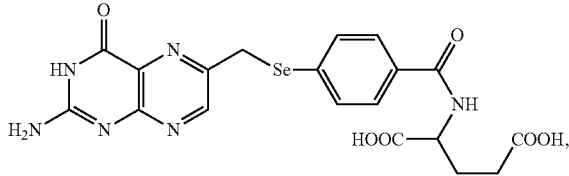

and a pharmaceutically acceptable salt, ester, stereoisomer, or solvate thereof.

The following examples relate to various methods of manufacturing certain specific compounds as described herein. All compound numbers expressed herein are with reference to the synthetic pathway figures shown above.

EXAMPLES

Example 1

The synthesized selenated folate hybrids (I-IV) are as shown below.

Synthesized selenated folate hybrids (I-IV).

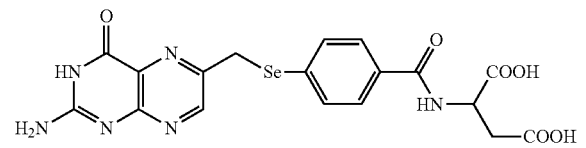

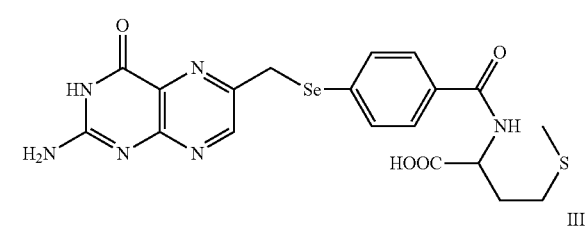

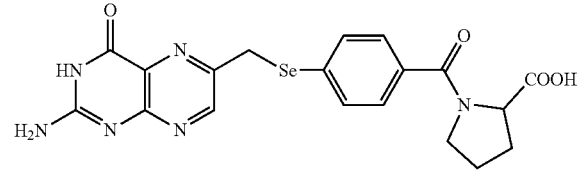

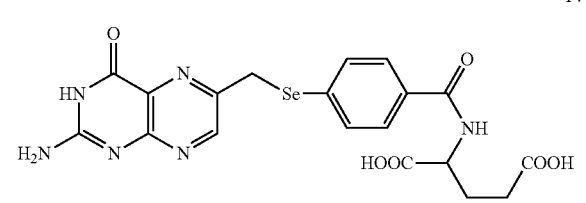

Compound 4-(((2-amino-4-oxo-3,4-dihydropteridin-6-yl)methyl)selanyl)benzoic acid (3) was synthesized by the reduction of 4,4'-diselanediyldibenzoic acid (2) using $NaBH_4$ under inert gas (e.g., $N_2$) in ethanol followed by subsequent reaction with 2-amino-6-(bromomethyl)pteridin-4(3H)-one (1) via nucleophilic substitution strategy.

The reaction of benzoic acid derivative 3 with oxalyl chloride in dichloromethane affords the respective acid chloride, which in turn reacts, in situ, with different amino acids, namely aspartic acid, L-methionine, glutamic acid, and proline to give the corresponding amides (4-(((2-amino-4-oxo-3,4-dihydropteridin-6-yl)methyl)selanyl)benzoyl)aspartic acid (4), (4-(((2-amino-4-oxo-3,4-dihydropteridin-6-yl)methyl)selanyl)benzoyl)methionine (5), (4-(((2-amino-4-oxo-3,4-dihydropteridin-6-yl)methyl)selanyl)benzoyl) glutamic acid (6), and (4-(((2-amino-4-oxo-3,4-dihydropteridin-6-yl)methyl)selanyl)benzoyl)proline (7) as depicted in the following Scheme:

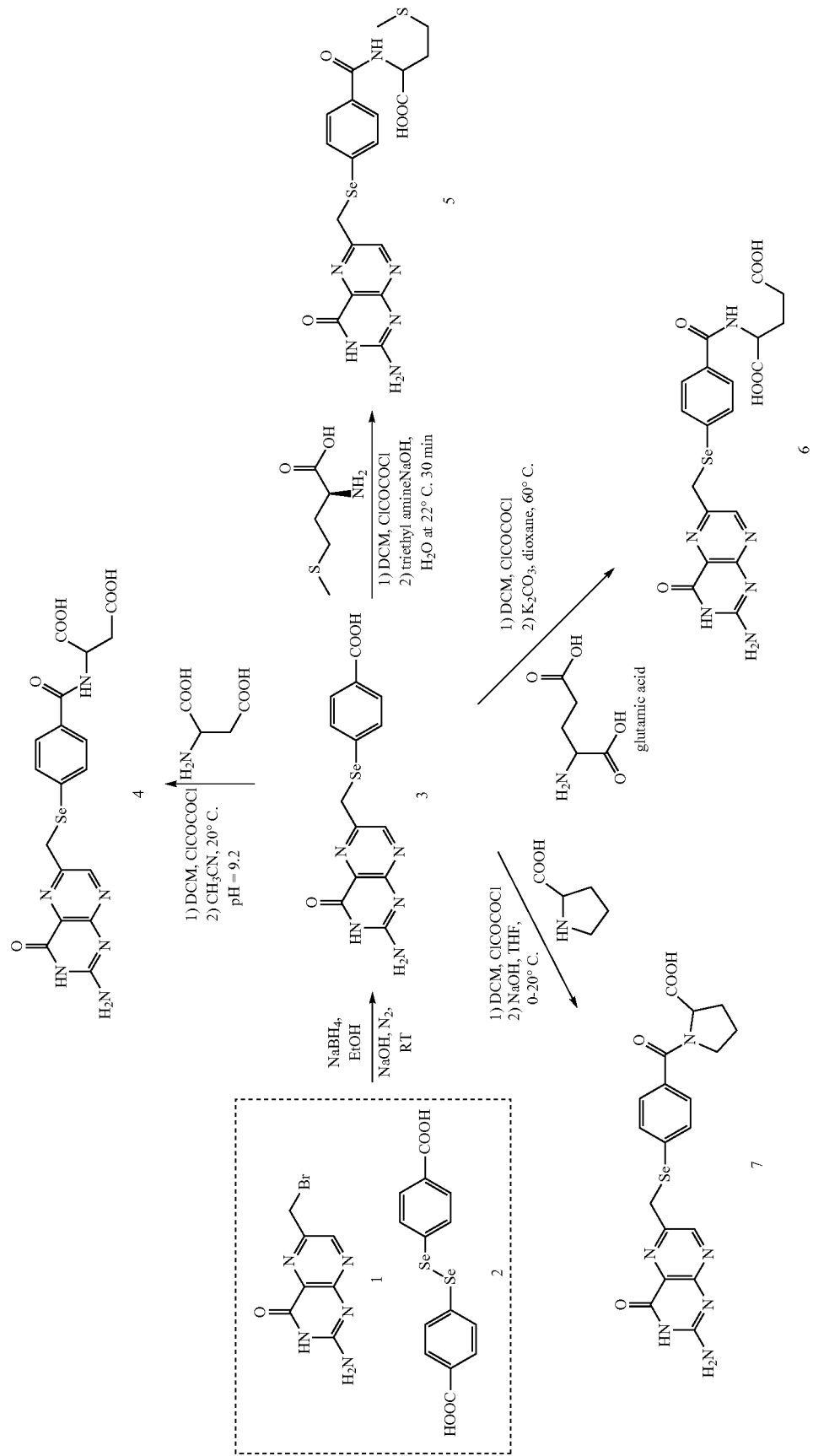

It is to be understood that the organic selenide compounds and the use thereof are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound of formula I:

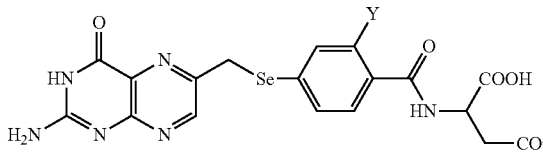

I or a pharmaceutically acceptable salt, ester, stereoisomer, or solvate thereof, wherein:
Y is selected from the group consisting of hydrogen, fluorine, $NO_2$, methyl, and cyano.
2. A compound of formula II:

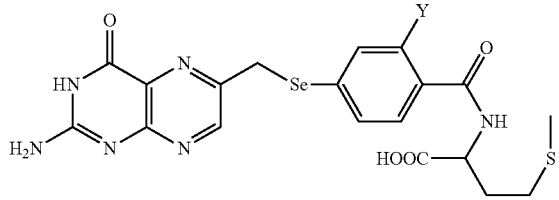

II it or a pharmaceutically acceptable salt, ester, stereoisomer, or solvate thereof, wherein:
Y is selected from the group consisting of hydrogen, fluorine, $NO_2$, methyl, and cyano.
3. A compound of formula III:

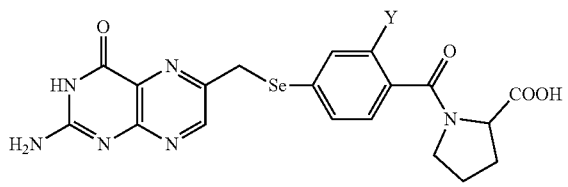

III or a pharmaceutically acceptable salt, ester, stereoisomer, or solvate thereof, wherein:
Y is selected from the group consisting of hydrogen, fluorine, $NO_2$, methyl, and cyano.

4. A compound of formula IV:

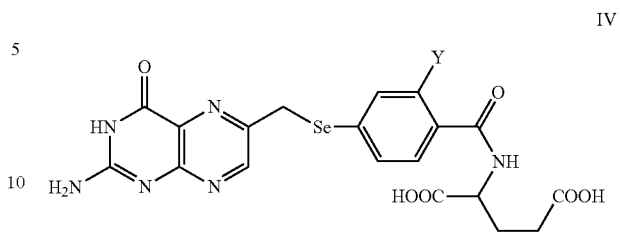

IV or a pharmaceutically acceptable salt, ester, stereoisomer, or solvate thereof, wherein:
Y is selected from the group consisting of hydrogen, fluorine, $NO_2$, methyl, and cyano.
5. A compound selected from the group consisting of:

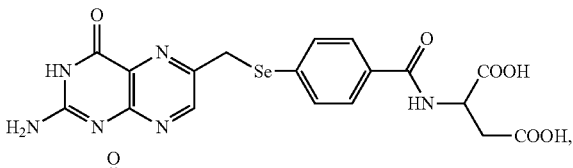

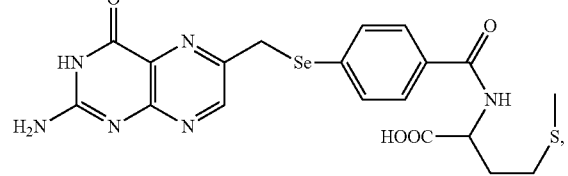

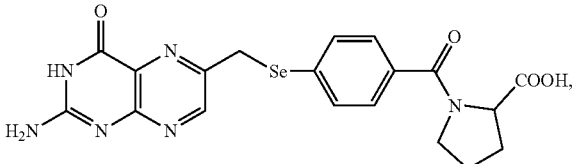

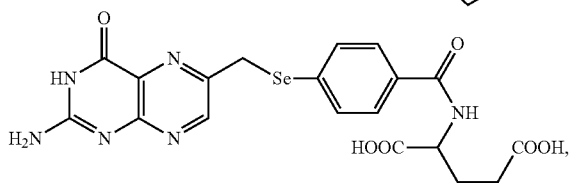

and a pharmaceutically acceptable salt, ester, stereoisomer, or solvate thereof.
6. A pharmaceutical composition comprising a compound of claim 5 and a pharmaceutically acceptable carrier.
7. A pharmaceutical composition comprising a compound of claim 1 and a pharmaceutically acceptable carrier.
8. A pharmaceutical composition comprising a compound of claim 2 and a pharmaceutically acceptable carrier.
9. A pharmaceutical composition comprising a compound of claim 3 and a pharmaceutically acceptable carrier.
10. A pharmaceutical composition comprising a compound of claim 4 and a pharmaceutically acceptable carrier.

* * * * *